United States Patent

Boussignac et al.

[11] Patent Number: 6,059,808
[45] Date of Patent: May 9, 2000

[54] IMPLANTABLE DEVICE AND DELIVERY SYSTEM TO REESTABLISH OR MAINTAIN A BODILY CANAL

[75] Inventors: Georges Boussignac, Antony; Pierre Hilaire, Paris, both of France

[73] Assignee: Laboratoires Nycomed SA, Paris, France

[21] Appl. No.: 08/838,772

[22] Filed: Apr. 10, 1997

[30] Foreign Application Priority Data

Apr. 10, 1996 [FR] France .................................. 96/04443

[51] Int. Cl.[7] .................................................. A61M 29/00
[52] U.S. Cl. ............................................ 606/191; 606/194
[58] Field of Search ................................... 606/191, 192, 606/193, 194, 195; 604/96; 623/11, 12, 1

[56] References Cited

U.S. PATENT DOCUMENTS

| | | | |
|---|---|---|---|
| 4,733,665 | 3/1988 | Palmaz | 128/343 |
| 4,739,762 | 4/1988 | Palmaz | 128/343 |
| 4,800,882 | 1/1989 | Gianturco | 128/343 |
| 4,886,062 | 12/1989 | Wiktor | 128/343 |
| 4,907,336 | 3/1990 | Gianturco | 29/515 |
| 5,133,732 | 7/1992 | Wiktor | 606/195 |
| 5,304,194 | 4/1994 | Chee et al. | 606/191 |
| 5,314,472 | 5/1994 | Fontain | 623/12 |
| 5,536,274 | 7/1996 | Neuss | 623/1 |

OTHER PUBLICATIONS

Safian, Robert D., M.D.; "Intracoronary Stents"; *Manual of Interventional Cardiology*; pp. 320–323, circa 1993.

*Primary Examiner*—Michael Buiz
*Assistant Examiner*—Vy Q. Bui
*Attorney, Agent, or Firm*—James J. Leary

[57] ABSTRACT

The subject of the present invention is an implantable device intended to reestablish or maintain the normal passage cross section of a bodily canal, of the type comprising an elongate framework which can expand radially between a first, contracted state of reduced diameter and a second, expanded state in which it has a diameter substantially equal to the natural diameter of said bodily canal and wherein said framework has, when contracted, at least one element consisting of a wire wound on itself, preferably with substantially constant pitch, along a substantially circular or helical directrix line.

22 Claims, 3 Drawing Sheets

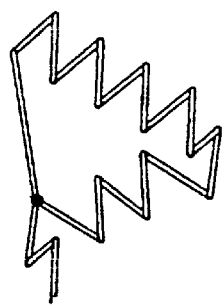
FIG.6D
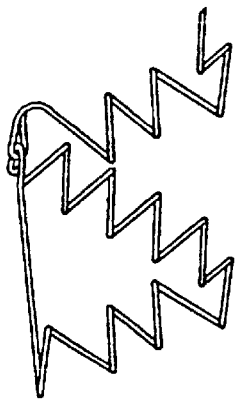
FIG.6C
FIG.6B
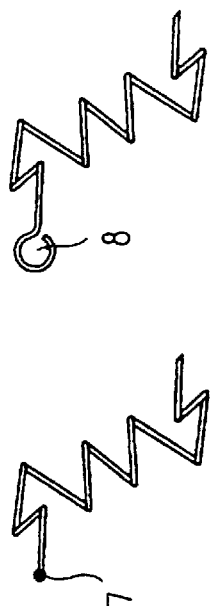
FIG.6A
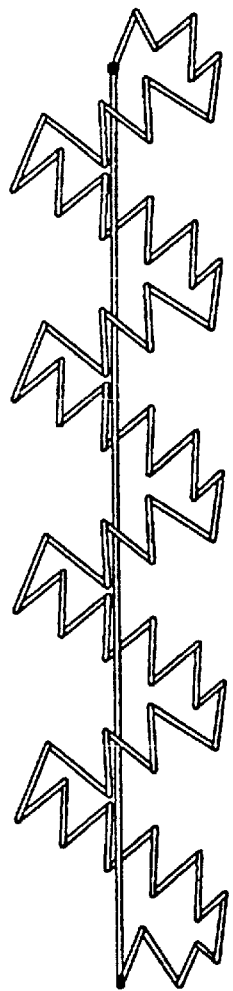
FIG.6E

IMPLANTABLE DEVICE AND DELIVERY SYSTEM TO REESTABLISH OR MAINTAIN A BODILY CANAL

FIELD OF THE INVENTION

The subject the present invention is an implantable device intended to maintain or reestablish the normal passage cross section of a bodily canal, as well as a system for fitting it.

The main application of the invention is in the field of treating blood vessels affected by stenosis.

It may also advantageously be used in the treatment of disorders of various canals in the human or animal body, such as, for example, the urinary canals and, in particular, the urethra, or else the digestive canals and, in particular, the esophagus.

BACKGROUND OF THE INVENTION

Strictures or stenoses of the blood canals (vessels, arteries or veins) cause serious circulation problems such as, in particular, atherosclerosis or phlebitis.

One method of treating such disorders conventionally consists in implanting, inside the canal affected by the stenosis, a device commonly referred to by the American term "stent", which is intended to reestablish or maintain the normal passage cross section of said canal at the stenosis.

The function of such a device is thus to serve as a prop for preventing the canal from reclosing spontaneously, or else to prevent its subsequent occlusion due to the development of the atheromatous disease.

The use of stents has become more widespread over the last few years, and very many devices have been proposed in the prior art.

These devices generally comprise an elongate framework which can expand radially between a first, contracted state of reduced diameter and a second, expanded state in which it has a diameter substantially equal to the natural diameter of said bodily canal to be treated.

Distinction is generally made between two broad categories of stents.

The first category includes autoexpansible stents, that is to say ones which can deploy, under their own action, from a first position, in which they are compressed contracted so as to allow introduction into the bodily canal, to a second, expanded position (for example by elastic expansion);

The second category includes stents whose expansion is mechanically forced, for example by means of a balloon dilation catheter.

The present invention more particularly relates to a device belonging to the latter category.

In their simplest design, devices belonging to this category consist of one or more elements formed by a deformable metal wire, with weak elastic memory, wound on itself, and forming a helical curve.

A more elaborate device is, for example, described in document EP-0,282,175.

It comprises a framework, also made from a deformable metal wire having a initial serpentine configuration, said serpentine configuration being shaped into a cylinder having a horizontal axis in order to form a radially expansible structure.

U.S. Pat. No. 4,886,062 describes a similar device to the latter, made from a wire having a flat "zigzagged" initial configuration, the zigzagged configuration being shaped into a cylinder by winding along a substantially helical curve.

All these known devices are therefore made from a wire which has a flat initial configuration which is subsequently shaped into a cylinder.

However, such configurations have a relatively limited capacity for expansion, leading to a degree of axial rigidity which makes them relatively difficult to use in twisted bodily canals such as, for example, the coronary arteries.

SUMMARY OF THE INVENTION

This being the case, the object of the present invention is to solve the technical problem of providing a device of the aforementioned type which is of novel design and has a capacity for expansion and an axial flexibility which are enhanced in comparison with devices known to date.

The object of the present invention is also to provide a device which can be produced easily on an industrial scale and which is easy to use.

According to the present invention, the solution for solving this technical problem consists of an implantable device intended to reestablish or maintain the normal passage cross section of a bodily canal such as, in particular, a blood vessel, of the type comprising an elongate framework which can expand radially between a first, contracted state of reduced diameter and a second, expanded state in which it has a diameter substantially equal to the natural diameter of the bodily canal, wherein said framework has, when contracted, at least one element consisting of a wire wound on itself, preferably with substantially constant pitch, along a substantially circular or helical directrix line.

As will be understood, the originality of the present invention resides in the three-dimensional initial configuration of each constituent element of the framework, in contrast to the (flat) two-dimensional initial configuration of the prior art devices.

This three-dimensional initial configuration of the wire makes it possible to obtain, in the contracted state, a device whose "turns" are fully contiguous, which results, for equal "contracted" size, in a capacity for expansion which is greatly superior to that of the prior art devices.

This enhanced capacity for expansion makes it possible to produce a framework which has excellent axial flexibility, irrespective of whether it consists of a single element wound on itself along a substantially helical directrix line, or of a plurality of elements, wound along a substantially circular directrix line and connected together, insofar as it is possible to form a relatively large space between each turn of said helix (in the case of a single element) or between two constituent elements (in the case of a plurality of elements).

Such a device according to the invention is particularly advantageous insofar as, when expanded, it has a very high degree of flexibility while retaining a very large measure of radial support.

According to a particular feature of the invention, the wire constituting each element of the aforementioned framework is made of a deformable metallic material, with weak shape memory.

Advantageously, such a material is chosen from the group comprising stainless steel, tungsten, platinum, tantalum and gold.

According to another particular feature of the invention, the wire constituting each element of the aforementioned framework is wound on itself and has a configuration similar to that of an optionally flattened helical spring.

According to a second aspect, the object of the present application is to encompass a system for fitting the aforementioned implantable device.

According to a particular feature, this system comprises a means for dilating the framework.

Advantageously, this dilation means consists of an inflatable catheter and the aforementioned framework is configured, in the contracted state, in such a way that said inflatable catheter can be received inside the framework while extending along its longitudinal axis.

According to a particular feature, the inflatable catheter is a catheter comprising a folded balloon.

BRIEF DESCRIPTION OF THE DRAWINGS

The invention will be better understood, and other objects, features and advantages thereof will appear more clearly, on reading the following explanatory description, made with reference to the appended schematic drawings which are given solely by way of nonlimiting example and illustrate a currently preferred embodiment of the invention, and in which:

FIGS. 6A, 6B, 6C, 6D and 6E represent various alternative embodiments of the end of the wire constituting each element of the framework of a device according to the invention.

DETAILED DESCRIPTION OF THE INVENTION

Figure 1:
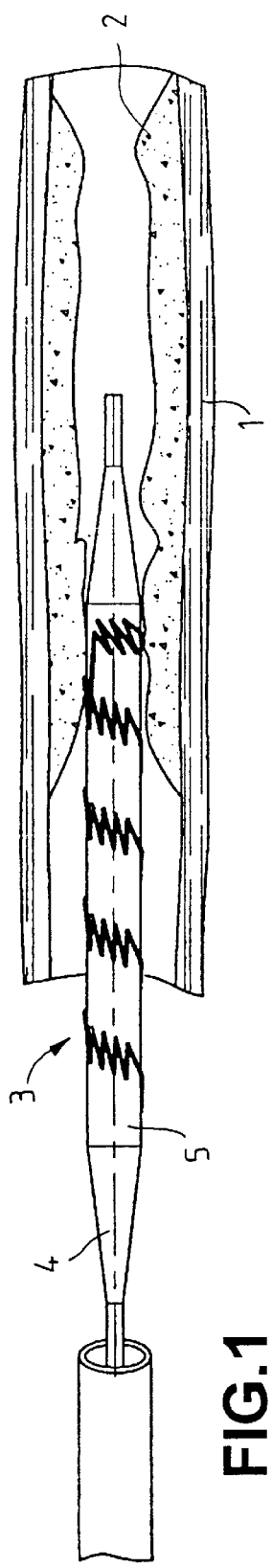
FIG. 1 is a schematic view in longitudinal section of an implantable device according to a currently preferred embodiment of the invention, and of the system for fitting it when it is contracted.

Thus, FIG. 1 represents an implantable device according to a currently preferred embodiment of the invention, as well as the system for fitting it.

The bodily canal chosen by way of example is a blood vessel 1 such as, in particular, a coronary artery which has a stenosis 2.

In the contracted state, represented in FIG. 1, a device according to the invention generally comprises a radially expansible elongate framework 3 comprising a single element consisting of a wire wound on itself, preferably with substantially constant pitch, along a substantially helical directrix line.

In other words, this structure results from a double winding of the wire, the primary winding defining a three-dimensional initial configuration whose advantages will be explained below.

The wire constituting the framework 3 is advantageously made of a deformable metallic material, with weak shape memory, so that the expansion of the framework can be mechanically forced, for example by means of a balloon dilation catheter.

Advantageously, such a metallic material may be chosen from the group comprising stainless steel, tungsten, platinum, tantalum and gold.

The framework 3 may consist, as in the example represented, of a single element, or of a plurality of elements connected together successively in pairs.

In the latter case, each element may be configured substantially in a "torus" by winding along a substantially circular directrix line.

The configuration of the primary winding of the wire on itself may be similar to that of a preferably flattened helical spring.

Figure 5C:
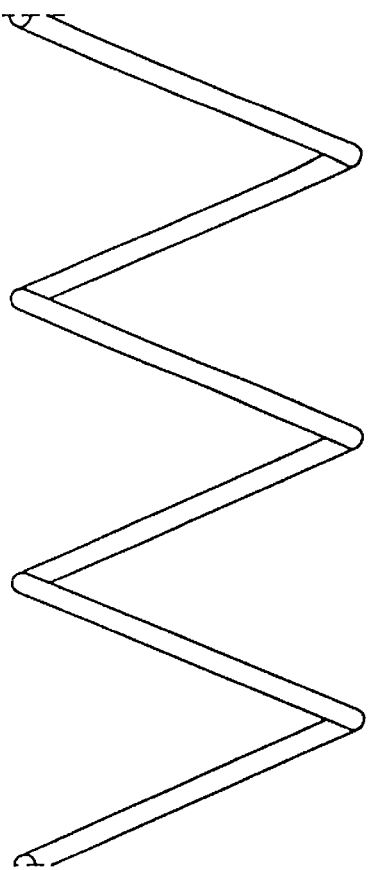
FIG. 5C is a front view, similar to FIG. 4C, of a device according to the present invention when it is expanded.
Figure 5B:
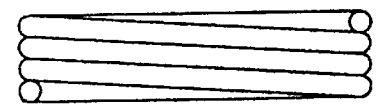
FIG. 5B is a front view, similar to FIG. 4B, of a device according to the present invention when it is contracted.
Figure 5A:
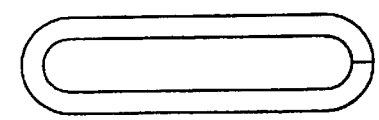
FIG. 5A is a side view, similar to FIG. 4A, of a device according to the present invention.

Thus, each turn of the primary winding may have a shape which is substantially circular, or else oval as represented in FIG. 5A.

The cross section of the wire constituting each element of the framework 3 may further be rectangular, oval or preferably circular.

The system for fitting the framework 3 includes a means for dilating the framework, which is preferably an inflatable catheter, generally denoted by the reference number 4 and comprising an inflatable balloon 5.

In the contracted state, the framework 3 is configured in such a way that the inflatable catheter can be received therein while extending along its longitudinal axis.

Figure 2:
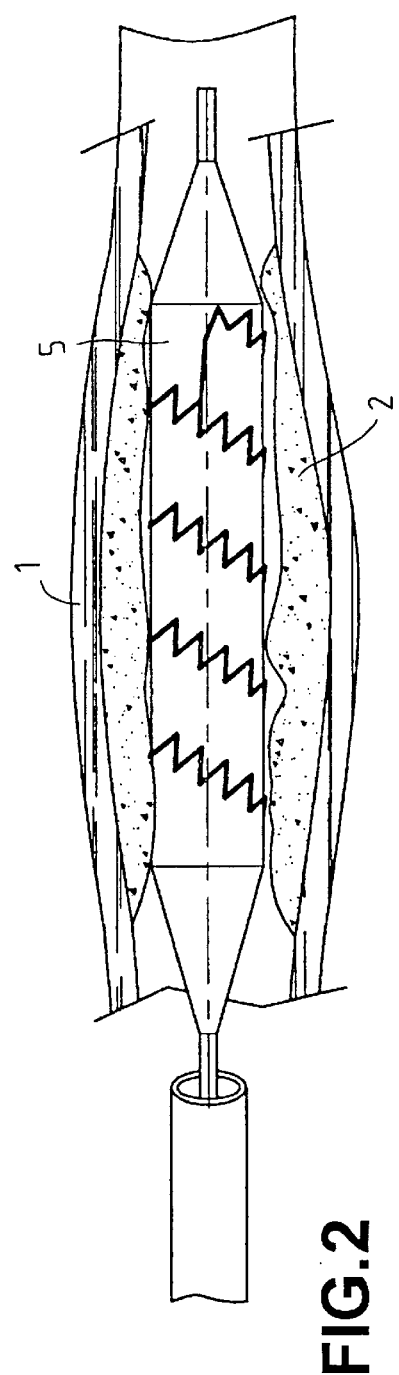
FIG. 2 is a similar view to FIG. 1, of the same device and of the system for fitting it when it is being expanded.

The framework 3 can be expanded, in mechanically forced fashion, by inflating the balloon 5 to a state in which it has a diameter substantially equal to the natural diameter of the bodily canal 1 (see FIG. 2).

Because the material constituting the wire has a weak shape memory, the framework 3 can then remain in its expanded position.

The system for fitting it can then be withdrawn, as will be understood, after deflating the balloon 5.

Figure 3:
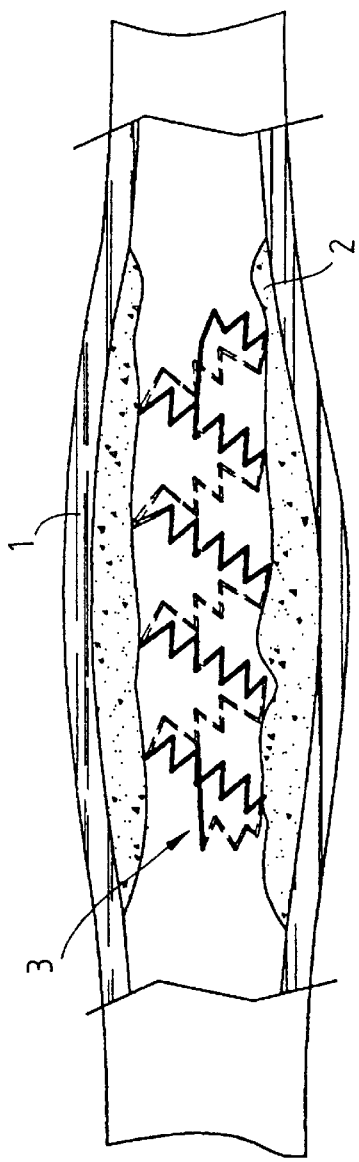
FIG. 3 is a similar view to FIGS. 1 and 2, showing the implantable device according to the present invention when it is expanded.

The configuration represented in FIG. 3 is thus obtained.

In order to more clearly demonstrate the originality of the present invention in comparison with the prior art devices, various views have been represented, making it possible to make a comparison between a device according to a currently preferred embodiment of the invention and a prior art device such as, for example, the one described in U.S. Pat. No. 4,886,062, made from a wire having a flat "zigzagged" initial configuration.

Figure 4C:
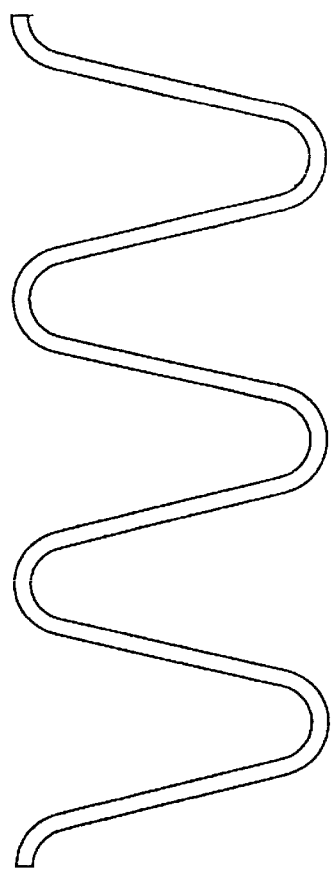
FIG. 4C is a front view of the same device, when it is expanded.
Figure 4B:
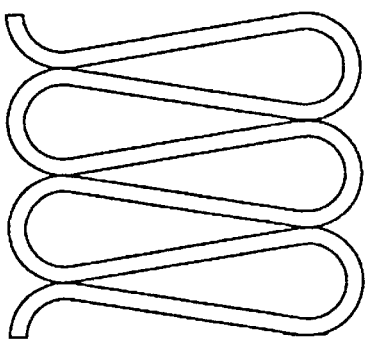
FIG. 4B is a front view of the same device, when it is compressed.
Figure 4A:
FIG. 4A represents a side view of an implantable device according to the prior art, in its zigzagged initial configuration.

Comparison of the prior art device in FIG. 4A and the present invention in FIG. 5A demonstrates the three-dimensional initial configuration of the device according to the invention, in contrast to the flat or two-dimensional initial configuration of the prior art device.

Comparison of the prior art device in FIG. 4B and the present invention in FIG. 5B immediately demonstrates the compact size, in the contracted state, of the device according to the invention in comparison with a prior art device.

As can be seen, the turns constituting the primary winding of the framework of the device according to the invention are fully contiguous, which significantly reduces its size.

Comparison of the prior art device in FIG. 4C and the present invention in FIG. 5C demonstrates the enhanced capacity of the device according to the invention for expansion.

Indeed, the expansion of the wire constituting the framework of a device according to the prior art takes place only by means of flexural deformation.

In contrast, the expansion of the wire constituting the device according to the present invention takes place by means of torsional deformation.

As will be understood, for the same contracted size, the device according to the present invention has a capacity for expansion which is greatly superior to that of the prior art devices.

This enhanced capacity for expansion can be used to give the device according to the present invention an axial flexibility which cannot be obtained with the prior art devices.

As shown by FIG. 3, the space separating two consecutive turns of a device according to the present invention may be relatively large while making it possible to retain a high degree of strength of the framework under compression.

For the same contracted size, the consecutive turns of a prior art device are virtually contiguous in the expanded state, and as will be understood, this impairs the axial flexibility of the structure.

In addition, for the same degree of expansion, the device according to the present invention requires less metallic material to produce it than a prior art device.

The enhanced capacity of the device according to the present invention for expansion is therefore particularly advantageous since it makes it possible, for a given degree of expansion, to reduce the quantity of foreign matter in the body, in comparison with the prior art device.

The end of the wire constituting each element of the framework 3 of an implantable device according to the present invention may have various forms.

This end may, for example, have the form of a microsphere 7 (FIG. 6A) or may alternatively be folded back on itself in a substantially circular shape 8 (FIG. 6B).

According to an alternative embodiment, the end of the wire constituting the framework 3 can be connected to the preceding helix turn by being folded back, as represented in FIG. 6C, or by welding, as represented in FIG. 6D.

Finally, according to yet another alternative embodiment, the two ends of the wire constituting the framework 3 may be connected together along an axis substantially parallel to the longitudinal axis of the framework (FIG. 6E).

The device which has just been described can be fitted in a manner known per se, and reference may in this regard be made to the prior art documents and, in particular, to U.S. Pat. No. 4,886,062, which is hereby incorporated by reference in its entirety.

The device according to the present invention may further be applied or used for fixing implants, in particular cardiac valves or elastic membranes for aneurysm isolation.

We claim:

1. An implantable device intended to reestablish or maintain the normal passage cross section of a bodily canal comprising an elongate framework which can expand radially between a first, contracted state of reduced diameter and a second, expanded state in which it has a diameter substantially equal to the natural diameter of the bodily canal, wherein said framework has, when contracted, at least one element consisting of a wire wound on itself along a substantially circular or helical directrix line, wherein the wire constituting each element of said framework is made of a deformable metallic material with a weak shape memory, wherein the wire constituting each element of said framework is wound into a helical spring having coils that are substantially contiguous with one another when said framework is in the first, contracted state, and wherein said coils are spaced apart from one another when said framework is in the second, expanded state.

2. The device as claimed in claim 1, wherein said implantable device is configured for insertion and expansion within a blood vessel.

3. The device as claimed in claim 1, wherein said wire is wound on itself with substantially constant pitch.

4. The device as claimed in claim 1, wherein said deformable metallic material is selected from the group consisting of stainless steel, tungsten, platinum, tantalum and gold.

5. The device as claimed in claim 1, wherein the wire constituting each element of said framework is wound on itself and has a configuration of a flattened helical spring.

6. A system to reestablish or maintain the normal passage cross section of a bodily canal comprising:

an implantable device comprising an elongate framework that can be expanded radially from a first, contracted state of reduced diameter to a second, expanded state in which it has a diameter substantially equal to the natural diameter of the bodily canal, wherein said framework has, when contracted, at least one element consisting of a wire wound on itself along a substantially circular or helical directrix line, and wherein the wire constituting each element of said framework is wound into a helical spring having coils that are substantially contiguous with one another when said framework is in the first, contracted state, and wherein said coils are spaced apart from one another when said framework is in the second, expanded state; and a means for expanding said framework.

7. The system as claimed in claim 6, wherein said means for expanding said framework is an inflatable catheter, and wherein said framework is configured, in the first, contracted state, in such a way that said inflatable catheter can be received inside said framework while extending along its longitudinal axis.

8. The system as claimed in claim 6, wherein the inflatable catheter is a catheter comprising a folded balloon.

9. The system as claimed in claim 8 wherein the wire constituting each element of said framework is made of a deformable metallic material with a weak shape memory.

10. The system as claimed in claim 9, wherein said deformable metallic material is selected from the group consisting of stainless steel, tungsten, platinum, tantalum, gold and alloys thereof.

11. An implantable device intended to reestablish or maintain the normal cross section of a passage within a body canal comprising a framework which can expand radially between a first, contracted state of reduced diameter and a second, expanded state in which it has a diameter substantially equal to the natural diameter of the body canal, wherein said framework has at least one element which, when in the first, contracted state, follows a primary winding that defines a three-dimensional initial configuration, said primary winding of said at least one element being configured into a secondary winding that defines a substantially cylindrical shape, wherein said primary winding has coils that are substantially contiguous with one another when said framework is in the first, contracted state, and wherein said coils are spaced apart from one another when said framework is in the second, expanded state.

12. The device as claimed in claim 11, wherein said secondary winding follows a substantially helical curve.

13. The device as claimed in claim 11, wherein said primary winding follows a substantially helical curve.

14. The device as claimed in claim 11, wherein said primary winding follows a flattened helical curve.

15. The device as claimed in claim 11, wherein said at least one element is made of a material having a weak shape memory.

16. The device as claimed in claim 11, wherein said at least one element is formed of a wire made of a deformable metallic material.

17. The device as claimed in claim 16, wherein said deformable metallic material is selected from the group consisting of stainless steel, tungsten, platinum, tantalum, gold and alloys thereof.

18. An implantable device intended to reestablish or maintain the normal cross section of a passage within a body canal comprising a framework which can expand radially between a first, contracted state of reduced diameter and a second, expanded state in which it has a diameter substantially equal to the natural diameter of the body canal, wherein said framework has at least one element which, when in the first, contracted state, follows a primary winding that defines a helical curve, said primary winding of said at least one element being configured into a secondary winding that defines a second, substantially helical curve when said framework is in the first, contracted state, and that defines a larger diameter helical curve when said framework is in the second, expanded state, wherein said primary winding has coils that are substantially contiguous with one another when said framework is in the first, contracted state and wherein said coils are spaced apart from one another when said framework is in the second, expanded state.

19. The device as claimed in claim 18, wherein said at least one element is made of a material having a weak shape memory.

20. The device as claimed in claim 18, wherein said at least one element is formed of a wire made of a deformable metallic material.

21. The device as claimed in claim 20, wherein said deformable metallic material is selected from the group consisting of stainless steel, tungsten, platinum, tantalum, gold and alloys thereof.

22. The device as claimed in claim 18 wherein said primary winding defines a flattened helical curve when said framework is in the first, contracted state.

* * * * *